United States Patent [19]

Arney et al.

[11] Patent Number: 4,896,547
[45] Date of Patent: Jan. 30, 1990

[54] AIR-SAMPLING APPARATUS WITH EASY WALK-IN ACCESS

[75] Inventors: Michel D. Arney, Roslindale; Gianfranco Zaccai, Boston; Eugene K. Achter, Lexington; Edward J. Burke, Waltham; Gabor Miskolczy, Carlisle; Ain A. Sonin, Lexington, all of Mass.

[73] Assignee: Thermedics Inc., Woburn, Mass.

[21] Appl. No.: 272,951

[22] Filed: Nov. 18, 1988

[51] Int. Cl.$^4$ .............................................. G01N 1/14
[52] U.S. Cl. ................................................ 73/863.81
[58] Field of Search ................. 73/23, 863.11, 863.31, 73/863.33, 863.81, 863.83, 863.84, 863.86, 864, 864.81; 340/632, 633, 634

[56] References Cited

U.S. PATENT DOCUMENTS

| | | | |
|---|---|---|---|
| 3,765,842 | 10/1973 | Purt | 340/633 |
| 3,998,101 | 12/1976 | Bradshaw et al. | 73/864 |
| 4,045,997 | 9/1977 | Showalter et al. | 73/23 |
| 4,202,200 | 5/1980 | Ellson | 73/23 |
| 4,718,268 | 1/1988 | Reid et al. | 73/864 |
| 4,736,637 | 4/1988 | Stock | 73/863.83 |
| 4,813,984 | 3/1989 | Griffis | 73/863.31 |

OTHER PUBLICATIONS

Lourence et al., "Flexible Bags Collect Gas Samples", Control Engineering, Sep. 1967, p. 105.
Spangler, G. E. et al., "Analysis of Explosives and Explosive Residues with Ion Mobility Spectrometer (IMS)", Mar. 29-31, 1983, pp. 267-282.

Primary Examiner—Robert R. Raevis
Attorney, Agent, or Firm—Herbert E. Messenger

[57] ABSTRACT

Disclosed is a walk-in inspection apparatus for active production of air samples containing vapors of explosives, drugs, or other substances carried by a person. The apparatus includes a U-shaped booth with an open end through which a person walks past walls which may contain a metal detector, then stands in front of a mesh screen facing a vertical end wall containing a vertical array of shaped funnels. Light-transmissive wall sections near the end wall help encourage entry of the person into the booth, and the light colored mesh screen draws attention of a person in the booth away from the darker funnels. In the collection of an air sample a blower outside the booth sucks a large volume of air around the person and horizontally through the funnels in the end wall and through ducts into a collection manifold for subsequent analysis. During sampling, infrared heaters in the end wall heat the clothing and skin of the person and many small nozzles extending through the end wall direct pulsed jets or puffs of air at the person to dislodge vapors, expel air from beneath clothing, and disrupt stagnant boundary layers of air near the person. Substantially all of the air drawn around the person is collected, and curved shapes of portions of the booth, funnels, and ducts provide smooth, low loss airflow to the collection manifold.

3 Claims, 5 Drawing Sheets

AIR-SAMPLING APPARATUS WITH EASY WALK-IN ACCESS

This invention was made with Government support under Contract No. DTR5-57-84-C-00063 awarded by the Department of Transportation. The Government has certain rights in this invention.

BACKGROUND OF THE INVENTION

This invention relates to apparatus for inspection of persons and more particularly to a walk-in inspection apparatus for producing air samples containing vapors of selected compounds such as explosives or drugs carried by a person.

Systems are known for acquiring air samples from subjects for detection of substances which emit vapors. For example, U.S. Pat. No. 4,202,200 describes apparatus for detecting explosives including an open-ended tunnel with two opposed pairs of apertures spaced at different distances along the tunnel walls. Air is circulated across the tunnel and through ducts connecting the apertures, and explosives detectors in one or more of the ducts detect vapors of explosives stripped from a person or vehicle positioned in, or passing through, the tunnel.

Systems of the type disclosed in the above-referenced U.S. Pat. No. 4,202,200 offer savings in time and labor when compared to hand-held sensors which are moved over a vehicle or the clothing of a person to be inspected. However, these automatic systems may result in the sampling of a non-representative portion of the air flowing past a subject, or the sampling of air flowed over less than the entire body of a person. Such incomplete sampling presents a risk of failure to detect concealed explosives or other substances. Also, the systems use similar arrangements for both vehicles and persons, and may be perceived as intimidating or quite uninviting places by people being screened. Moreover, diffusion of vapors into the collection air stream may be inadequate to provide samples containing concentrations of substances sufficient for their detection.

An object of the present invention is to provide an improved walk-in system for producing air samples by flowing air over, and collecting it from, essentially the entire body of a person during screening for selected vapor-emitting materials.

It is an object of the invention to provide a walk-in apparatus which minimizes the inconvenience to persons being sampled.

It is an object of the invention to provide apparatus for producing air samples including a walk-in booth which persons to be screened perceive as non-threatening and as inviting entry.

SUMMARY OF THE INVENTION

The invention is a walk-in inspection apparatus for producing air samples containing vapors of selected compounds carried by a person, particularly materials such as explosives, heroin, or cocaine, and which includes features which encourage or facilitate its use by persons to be inspected. The inspection system of the invention includes a U-shaped booth with an open end for walk-in entry of a person, and devices for actively producing and collecting an air sample from air flowed in contact with a person standing near an end wall of the booth. Exit of the person from the booth may be either through the open end or through a door in a side wall.

In a preferred embodiment the side walls and top of the booth of the inspection apparatus include sections near its curved end wall which are formed of clear plastic or glass. The front portions near the open end of the booth are opaque, and the resulting dark/light contrast encourages entry of a person into the booth for screening.

Within the booth several aerodynamically-shaped funnels are mounted in a vertical array near the center of its end wall. The funnels are connected to ducts leading to a collection manifold which in turn is connected to a suction blower outside of the booth. Heaters such as infrared lamps are positioned on either side of the funnel array to heat the clothing and skin of a person standing near the funnels, and air jet nozzles are mounted in the end wall to direct pulsed jets of air at a person standing in position to be inspected.

In the production of a sample by the inspection apparatus of the invention, a person walks into the booth and stands in position in front of a light-colored mesh screen near the funnels. With the suction blower, heat lamps, and air jet nozzles in operation, an air flow field is created, as determined by the curved shape of the closed end of the booth, the funnels, the air flow rate, and the presence of the person in the booth. Vapors stripped from the person, with the active assistance of the air puffs and heat, enter the flow field and are transported in an air sample through the funnels to the collection manifold. Subsequent analysis of the air sample produced by the inspection apparatus of the invention reveals the presence or absence of vapors of explosives, drugs, or other substances.

DETAILED DESCRIPTION OF PREFERRED EMBODIMENTS

The apparatus of the present invention is useful in producing, for subsequent analysis in an appropriate detector, air samples of certain substances which give off vapors and which are carried by persons—i.e., concealed on a person or present on or within the person's clothing. Included among the substances of interest are explosives such as trinitrotoluene (TNT), dinitrotoluene (DNT), pentaerythritol tetranitrate (PETN), nitroglycerin (NG), cyclo 1,3,5-trimethylene-2,4,6 -trinitramine (RDX), and ammonium nitrate; drugs such as cocaine and heroin; and chemical warfare agents such as mustard gas and organo-phosphate compounds. For the purpose of this invention and the descriptions contained herein, "vapor" means not only vapors in the gas phase but also aerosols containing the substances of interest in dissolved form, and small mobile particles comprised of the substances themselves or on or within which the substances are trapped.

Figure 1:
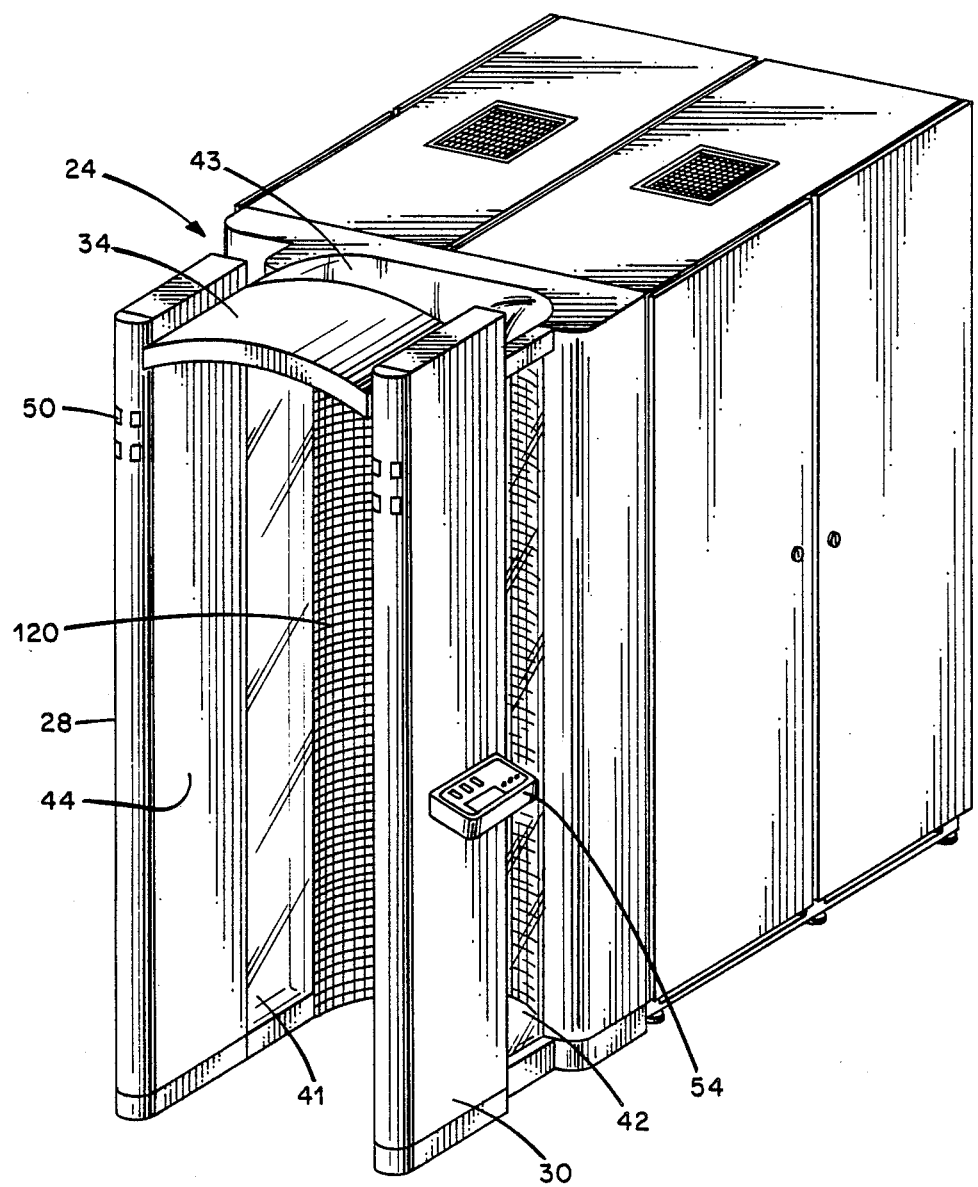
FIG. 1 is a perspective view of the walk-in inspection apparatus of the invention.
Figure 2:
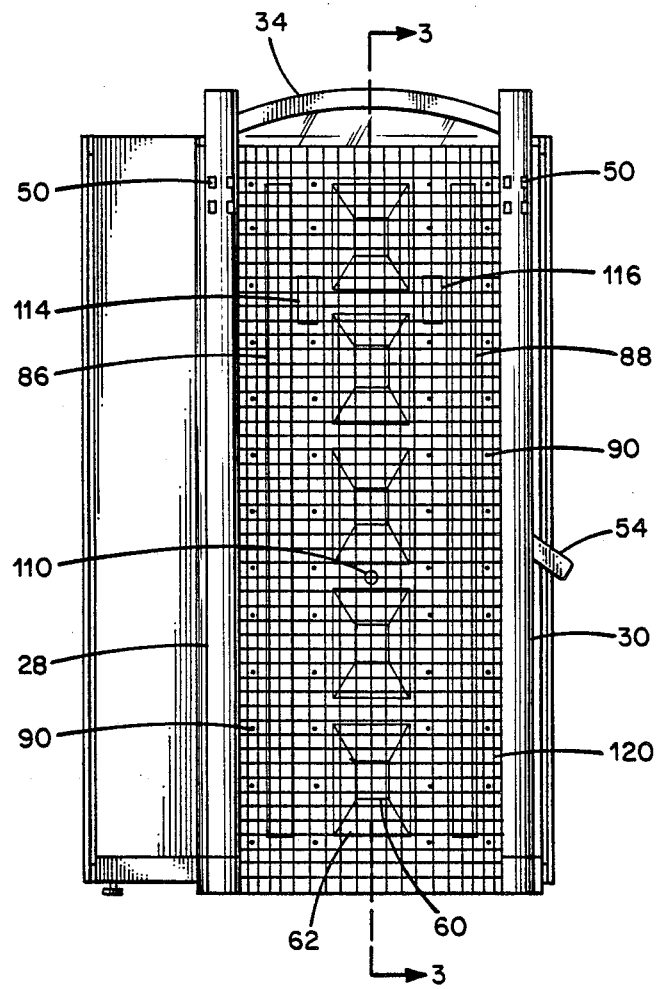
FIG. 2 is a front elevational view of the inspection apparatus of FIG. 1.

A preferred inspection apparatus 20 according to the invention (FIGS. 1-4) includes a walk-in booth 24 formed by two opposed side walls 28 and 30, a top 34, and an end wall 40. Except for the open front end through which a person may enter and leave the booth 24 and for passages formed in the end wall 40 to accommodate equipment described hereinafter, the booth 24 is substantially airtight when installed in an upright position on a floor or other horizontal surface (FIGS. 1 and 2). A typical inspection space defined by the walls and top is about 7 feet high by 2.5 feet wide by 3.75 feet deep.

To minimize feelings of confinement by a person within the booth 24, portions of its side walls 28 and 30 and of the top 34, particularly those near the end wall 40, may be illuminated or, more preferably, are formed of clear plastic or of glass. The clear or translucent portions, designated at sections 41, 42 and 43, also admit light from outside of the booth 24 and allow observation of the person being inspected from either side of the booth 24.

The illuminated or light-transmitting sections 41, 42, and 43 provide a further benefit associated with their contrast with the opaque front portions of the side walls 28, 30 and top 34 of the booth 24. Because the booth 24, when viewed from the front, has the appearance of a tunnel with light near its closed end, a person facing its open end perceives the booth as more inviting to enter than he/she would a uniformly illuminated booth or one whose front portions are lighter than, or offer little contrast with, rear portions. As a result the booth "draws" people in or lessens any uneasiness they might feel in entering for inspection.

Although not required for operation of the inspection apparatus in producing air samples from a person, the inspection apparatus 20 illustrated in FIGS. 1-4 includes a metal detector within the opposed panels 44 and 46 forming the front portion of the walk-in booth 24. The metal detector comprises conventional low level electromagnetic devices embedded in either or both panels 44 and 46. Also provided in the front edges of the wall panels 44 and 46 are lights 50 which may be of different colors for indicating whether the booth is unoccupied and available for entry of a person. The lights are electric-ally connected to an operator control panel 54 mounted on the outside of the side wall 30 and which may be used to display the condition and control the functioning of certain electrically-operable components of the inspection apparatus.

Figure 3:
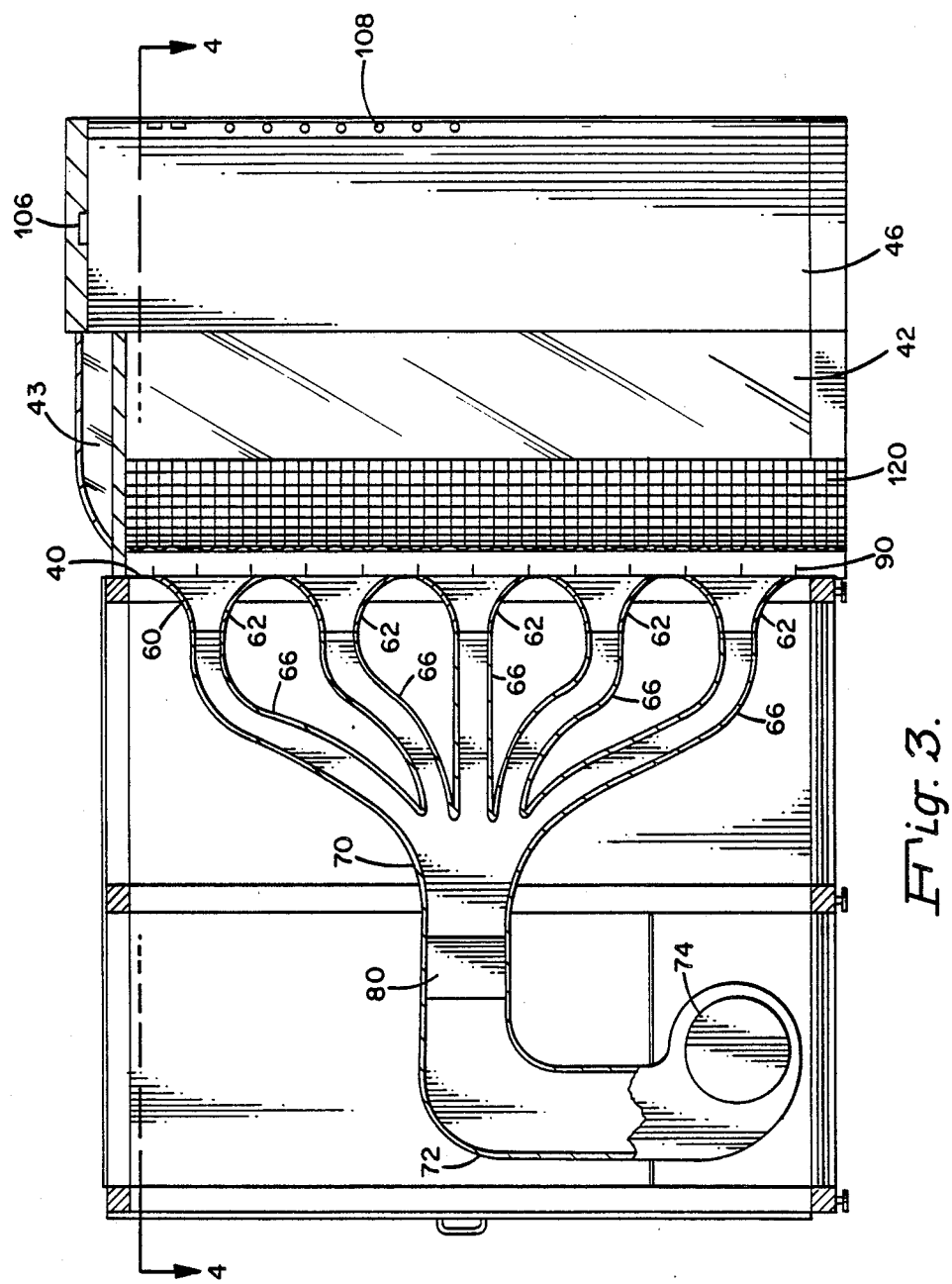
FIG. 3 is a side elevational view of the inspection apparatus taken along the line 3—3 of FIG. 2.

As best shown in FIGS. 2 and 3, the end wall 40 of the inspection booth 24 includes a vertical array of equally-spaced apertures 60 in which funnels or aerodynamically-shaped inlets 62 are mounted for withdrawal of air from the booth 24. The funnels 62, five being shown in FIGS. 2 and 3 by way of illustration, extend over the entire height of the inspection space defined by the end wall 40, so as to permit withdrawal of air in a substantially horizontal direction from around each exterior surface of a person standing in the booth 24. Behind the end wall 40 and within an enclosure 64 are collection ducts 66, with each having one end connected to the outlet of a funnel 62, and the opposite end connected to a collection manifold 70. The manifold 70 in turn is connected to a duct 72 leading to a fan or suction blower 74 which is operable to rapidly draw a large volume of air from within the booth 24 through the ducts 66, the collection manifold 70, and the duct 72. A vapor detector, indicated schematically at 80 though not forming part of the present invention, may be contained within, or extend into, the duct 72 between the manifold 70 and the blower 74 to detect specific vapors in the air sample. Although not shown, the duct 72 may contain a valve and side branch to bypass the vapor detector 80 so that the suction blower 74 may operate continuously regardless of whether air samples are being taken and directed into the vapor detector 80.

The instrument employed as the vapor detector 80 may be one of several different types, depending on the specific vapors to be identified in the air sample and the sensitivity and speed of detection required. For example, the vapor detector may be a mass spectometer, as described in U.S. Pat. No. 4,718,268, to Reid et al, which is operable to detect explosives and may also detect chemical warfare compounds. Other suitable instruments are detectors such as a flame ionization detector or a nitric oxide analyzer with a chemiluminescence detector as described in U.S. Pat. No. 4,301,114 to Rounbehler.

Figure 4:
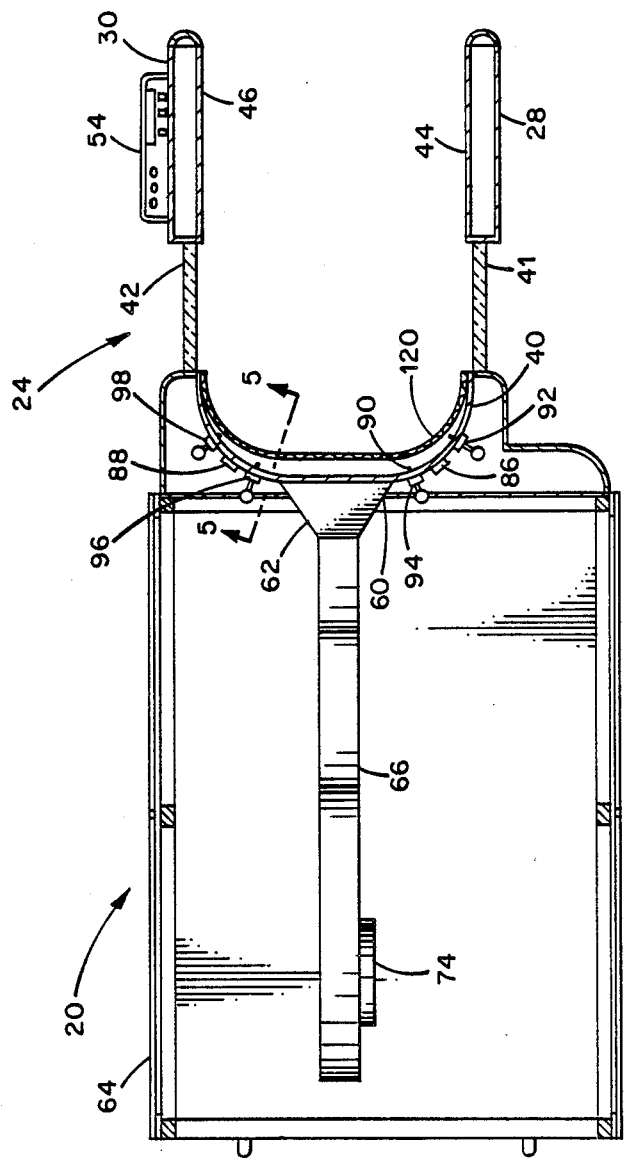
FIG. 4 is a top view of the inspection apparatus taken along the line 4—4 of FIG. 3.

Also mounted in the end wall 40 on each side of the funnels 62 are narrow strip heaters 86 and 88 which extend over a substantial portion of the height of the booth 24. The heaters 86 and 88, which preferably include electrically-powered infrared heating elements having little or no visible light output, are operable to heat the clothing and skin of a person standing at a designated position facing the end wall 40, as shown in FIG. 4. Heating raises the vapor pressure of explosives and/or other substances which may be concealed or present in trace quantities on the skin or clothing of the person. This enhances release of the substances into the flow field of air created by the blower 74 sucking an air sample through the funnels 62.

Figure 5:
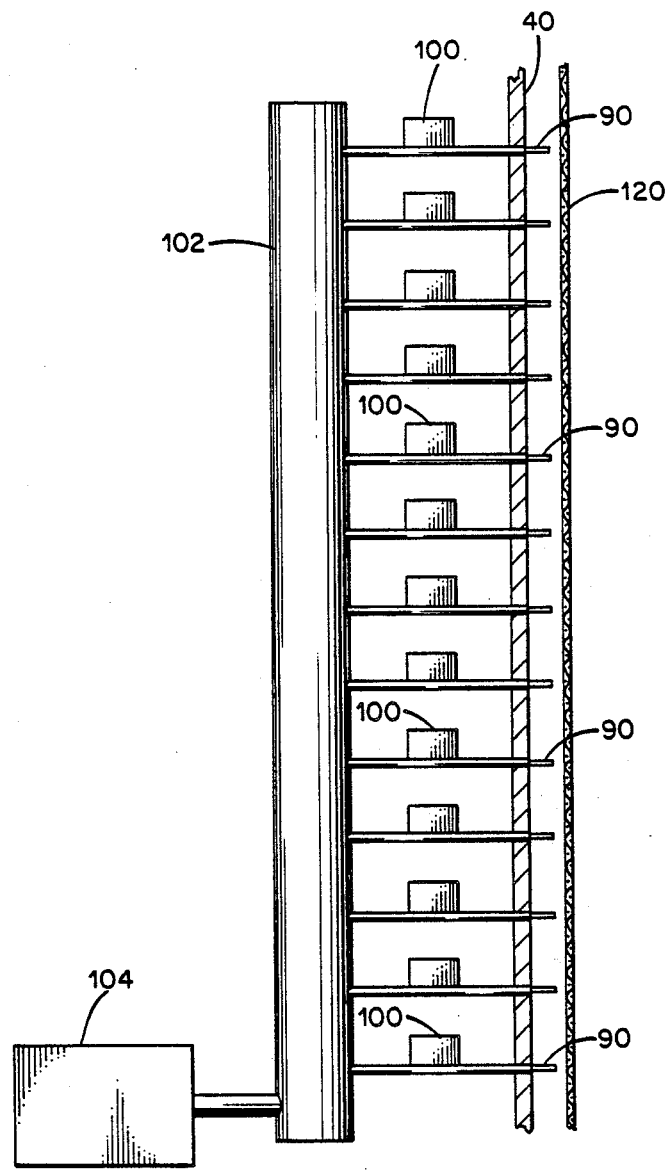
FIG. 5 is an elevational view taken along the line 5—5 of FIG. 3 and illustrating, in enlarged scale from that of FIG. 3, an array of air jet nozzles extending through the end wall of a booth forming part of the inspection apparatus.

As is best shown in FIGS. 2, 4, and in the enlarged elevational view of FIG. 5, arrays of air nozzles 90 also extend through the end wall 40. A preferred arrangement comprises a vertical column of spaced, small diameter nozzles on either side of each of the heaters 86 and 88 for a total of four columns 92, 94, 96, and 98. Each column includes several nozzles (e.g. 13 nozzles of 1/16 inch diameter—see FIG. 5) spaced several inches apart over a substantial portion of the height of the booth so as to direct jets of air at a person standing near the end wall 40. Each nozzle 90 in a column is in communication through a valve 100 with a reservoir of pressurized air such as a vertical pipe 102 which is connected to an air compressor 104 or other source of pressurized air. By rapid opening and closing of the valves 100, which may be solenoid valves operable automatically in a predetermined sequence, the nozzles 90 operate in a pulsed mode to deliver puffs or jets of air at relatively low volume and relatively high momentum. Sequential or staggered operation of the valves (rather than simultaneous operation) is preferred so as to maintain high pressure levels in the reservoir 102.

The puffs of air from the nozzles 90 shake the clothing of a person being inspected in the booth 24, thus releasing vapors of explosives and/or other substances, and also help expel air which may contain vapors from beneath the person's clothing. The air puffs also scrub vapors from exposed skin and enhance the effectiveness of air drawn over a person by breaking up or reducing the thickness of the stagnant boundary layer of air directly adjacent the skin and clothing of the person. A suitable series of air puffs for each nozzle 90 of the embodiment of the inspection apparatus shown and described herein is 5 puffs of approximately 0.1 second)

duration during a sample acquisition about 5 seconds in length.

To avoid discomfort which might arise from the impact of air jets in the face of a person being inspected, at least the upper nozzles 90 of each column 92, 94, 96, and 98 are electrically connected to a height sensor such as a sensor 106 mounted in the top 34 near the open end of the booth 24. Alternatively, each of selected upper nozzles 90 may be connected to one of a vertical array of height sensors 108 mounted in the panels 44 and 46 forming the front portion of the booth 24. These height sensors 108 may, for example, comprise an emitter/collector couple mounted in the panel 44 or 46 with a reflecting element positioned in the opposite panel. As a person walks into the booth 24, the height sensor determines the height of the person and suppresses subsequent operation of one or more nozzles whose air puffs would otherwise be directed into the face of the person.

As best shown in FIG. 4, the end wall 40 of the booth 24 includes curved portions where it joins the side walls 28 and 30. The top may also have a curved section near the end wall 40. The curved walls, and the streamlined shape of the funnels 62 through which air is withdrawn from the booth 24, results in a smooth, even flow of air around a person and into the collection manifold 70 during sampling. This permits large volumes of air and included vapors to be collected rapidly and without large flow losses. It also facilitates collection of air samples drawn over the complete exterior surface of a person so that no areas are missed where substances to be detected may be concealed. Moreover, the smooth flow substantially avoids contact of the air flow drawn from around a person with the walls of the booth. (Such contact could result in sticking and loss of vapors.)

The booth 24 also includes a sensor to determine the distance of a person from the end wall 40. A distance sensor 110 mounted near the center of the end wall 40 may be connected to indicator lights 114 and 116 in the end wall 40 and to audio equipment (not shown) in the booth 24 which instruct a person to walk into the booth for inspection and which also indicate whether the booth is occupied. For example, the indicator 114 may illuminate a walking symbol when the booth 24 is unoccupied and until a person enters and approaches close to a vertical mesh screen 120 near, but spaced from, its end wall 40. In response to a signal from the distance sensor 110, the indicator light 114 may then automatically switch off, the indicator light 116 may illuminate a "booth occupied" symbol, and a sampling sequence may be initiated utilizing air puffs from the nozzles 90, heat from the heaters 86 and 88, and air flow produced by the suction blower 74. The mesh screen 120 near the end wall 40 prevents a person from contact with the heaters 86, 88, the funnels 62, and the nozzles 90. Preferably the mesh screen 120 is lighter in color that the end wall 40 or the funnels 62 (which may be painted black) so as to preferentially attract the attention of a person facing the screen 120. This contrast lessens any uneasiness or discomfort associated with undue notice of the sampling equipment mounted within the end wall 40.

During operation of the sampling system 20 a person enters the unoccupied booth 24 by walking into its open end. The person is first screened for the presence of metal objects and, provided no alarm is activated by a metal detector in the panels 44 and 46, approaches the end wall 40 and halts near the mesh screen 120 facing the end wall. A sampling sequence of about 5 seconds duration is automatically initiated in response to a signal from the distance sensor 110, with air passed over the person and withdrawn through the funnels 62 into the collection manifold 70, and on into a suitable vapor detector 80. Active release of vapors from the skin and clothing of the person is promoted by heat from the heaters 86, 88 and air puffs from the nozzles 90 directed at the person. After sampling is complete, visual and/or audio instructions are given for the person to turn and walk out of the booth 24. (If desired, sampling may continue after the person has turned and is facing the open end of the booth). Finally, as the person is turning and walking out of the booth 24, the sample produced by the inspection system 20 may be analyzed in the vapor detector 80 for the presence of vapors of selected substances such as explosives, drugs, or chemical warfare compounds. If the sample is found to contain the target substance, the vapor detector may trigger an alarm in the inspection apparatus so that the person may be reinspected and/or detained and searched manually.

What is claimed is:

1. Apparatus for producing an air sample containing vapors of selected compounds carried by a person comprising:
    a booth sized to permit walk-in entry of a person and walk-out exit therefrom, said booth including a top, a pair of opposed generally vertical side walls, and a generally vertical end wall connected to said side walls and having at least one air passage therethrough;
    said booth having an open end opposite said end wall for walk-in entry of a person;
    portions of said side walls near the end wall of said booth being formed of light-transmissive materials and portions of said side walls and said top near the open end being opaque; and
    means for withdrawing air from within said booth through the air passage in said end wall, said air withdrawal means operable to cause air to flow from said open end over essentially the entire body of a person positioned within said booth and to produce an air sample containing vapors of said selected compounds removed from the person.

2. Apparatus as in claim 1 wherein said booth is U-shaped and portions of said end wall adjacent to said side walls form the curved portions of the U and are operable to facilitate the smooth flow of air during withdrawal of air from said booth.

3. Apparatus as in claim 1 wherein said end wall has a vertical array of air passages spaced one from another over a substantial portion of the height of the end wall, said air withdrawal means includes a shaped inlet extending through said end wall in each of said air passages and operable to receive a substantially horizontal flow of air from within the booth, and further including a generally vertical open-mesh screen positioned within said booth near said end wall, said screen being lighter in color than said end wall and said shaped inlets.

* * * * *